United States Patent
Rothgang

(10) Patent No.: US 9,326,701 B2
(45) Date of Patent: May 3, 2016

(54) METHOD AND MAGNETIC RESONANCE SYSTEM TO AUTOMATICALLY DETERMINE IMAGING PLANES

(71) Applicant: Eva Rothgang, Nuremberg (DE)

(72) Inventor: Eva Rothgang, Nuremberg (DE)

(73) Assignee: Siemens Aktiengesellschaft, Munich (DE)

(*) Notice: Subject to any disclaimer, the term of this patent is extended or adjusted under 35 U.S.C. 154(b) by 245 days.

(21) Appl. No.: 13/836,851

(22) Filed: Mar. 15, 2013

(65) Prior Publication Data
US 2013/0245427 A1   Sep. 19, 2013

(30) Foreign Application Priority Data

Mar. 16, 2012 (DE) .................. 10 2012 204 134

(51) Int. Cl.
| | | |
|---|---|---|
| *A61B 5/05* | (2006.01) | |
| *A61B 5/06* | (2006.01) | |
| *A61B 5/055* | (2006.01) | |
| *A61B 17/34* | (2006.01) | |
| *A61B 6/12* | (2006.01) | |
| *A61B 6/00* | (2006.01) | |

(Continued)

(52) U.S. Cl.
CPC .............. *A61B 5/061* (2013.01); *A61B 5/055* (2013.01); *A61B 6/12* (2013.01); *A61B 6/545* (2013.01); *A61B 17/3403* (2013.01); *G01R 33/285* (2013.01); *G01R 33/543* (2013.01); *A61B 6/032* (2013.01); *A61B 10/0233* (2013.01); *A61B 2019/5236* (2013.01); *A61B 2505/05* (2013.01)

(58) Field of Classification Search
CPC .......... A61B 5/061; A61B 6/12; A61B 6/545; A61B 17/3403; A61B 5/055; A61B 6/032; A61B 2019/5236; A61B 10/0233; A61B 2505/05; G01R 33/285; G01R 33/543
USPC .......................... 600/407–430; 382/128–132
See application file for complete search history.

(56) References Cited

U.S. PATENT DOCUMENTS

| | | | |
|---|---|---|---|
| 6,263,089 B1 * | 7/2001 | Otsuka ...................... | G06T 7/60 382/107 |
| 6,898,302 B1 * | 5/2005 | Brummer ................ | G06T 19/00 382/131 |

(Continued)

OTHER PUBLICATIONS

Ahrar et al., "Magnetic Resonance Imaging-Guided Laser Ablation of Bone Tumors," Tech. Vasc. Interv. Radiol., 2011, vol. 14(3), pp. 177-182.

(Continued)

*Primary Examiner* — Sanjay Cattungal
(74) *Attorney, Agent, or Firm* — Schiff Hardin LLP

(57) ABSTRACT

In a method and imaging apparatus to automatically determine imaging planes for an imaging procedure to visualize a percutaneous intervention of a patient along a trajectory to a target point, data are obtained that represent a reference coordinate system with three orthogonal reference planes, and data also are acquired that represent the trajectory. One of the reference planes is determined as a selected reference plane based on the arrangement thereof relative to the trajectory. A first imaging plane is defined such that the trajectory lies therein, and such that it has a defined arrangement in relation to the selected reference plane. A second imaging plane is defined such that the trajectory lies therein, and such that it is orthogonal to the first imaging plane. A third imaging plane is defined such that it is orthogonal to the first imaging plane and second imaging plane, and includes the target point.

23 Claims, 7 Drawing Sheets

(51) Int. Cl.
*G01R 33/28* (2006.01)
*G01R 33/54* (2006.01)
*A61B 10/02* (2006.01)
*A61B 19/00* (2006.01)
*A61B 6/03* (2006.01)

(56) References Cited

U.S. PATENT DOCUMENTS

| | | | | |
|---|---|---|---|---|
| 7,835,780 | B1* | 11/2010 | Duerk | G01R 33/287 600/410 |
| 8,585,598 | B2* | 11/2013 | Razzaque | A61B 19/5244 600/411 |
| 2001/0039378 | A1* | 11/2001 | Lampman | A61B 5/0555 600/410 |
| 2002/0156365 | A1* | 10/2002 | Tsekos | A61B 5/0555 600/411 |
| 2006/0050945 | A1* | 3/2006 | Lehtonen-Krause | G06T 7/0012 382/132 |
| 2007/0055131 | A1 | 3/2007 | Deinzer et al. | |
| 2008/0071163 | A1* | 3/2008 | Zhang | A61B 5/055 600/410 |
| 2008/0285829 | A1* | 11/2008 | Wang | A61B 5/055 382/131 |
| 2008/0292048 | A1* | 11/2008 | Haras | A61B 6/032 378/20 |
| 2010/0312094 | A1 | 12/2010 | Guttman et al. | |
| 2010/0312095 | A1* | 12/2010 | Jenkins | A61B 5/418 600/411 |
| 2011/0137156 | A1 | 6/2011 | Razzaque et al. | |
| 2012/0041311 | A1 | 2/2012 | Gades | |
| 2013/0195313 | A1 | 8/2013 | Gauthier et al. | |

OTHER PUBLICATIONS

Boll et al., "Low-Flow Vascular Malformations: MR-guided Percutaneous Sclerotherapy in Qualitative and Quantitative Assessment of Therapy and Outcome," Radiology, 2004, vol. 233(2), pp. 376-384.
Busse et al., "Flexible Add-on Solution for MR Image-Guided Interventions in a Closed-Bore Scanner Environment," Magnetic Resonance in Medicine, 2010, vol. 64(3), pp. 922-928.
Fischbach et al., "MR-Guided Freehand Biopsy of Liver Lesions With Fast Continuous Imaging Using a 1.0-T Open MRI Scanner: Experience in 50 Patients," Cardiovasc Intervent Radiol, 2011, vol. 34(1), pp. 188-192.
Fritz et al., "Diagnostic and Interventional MRI of the Sacroiliac Joints Using a 1.5-T Open-Bore Magnet: A One-Stop-Shopping Approach," Am. J. Roentgenol, 2008, vol. 191(6), pp. 1717-1724.
Fritz et al., "Freehand Real-Time MRI-Guided Lumbar Spinal Injection Procedures at 1.5 T: Feasibility, Accuracy, and Safety," Am. J. Roentgenol, 2009, vol. 192(4), pp. W161-W167.
Hayashi et al., "Hemangiomas in the Face and Extremities: MR-guided Sclerotherapy—Optimization with Monitoring of Signal Intensity Changes in Vivo," Radiology, 2003, vol. 226(2), pp. 567-572.
Ladd et al., "Biopsy Needle Susceptibility Artifacts," Magn. Reson. Med., 1996, vol. 36(4), pp. 646-651.
Lewin et al., "Needle Localization in MR-Guided Biopsy and Aspiration: Effects of Field Strength, Sequence Design, and Magnetic Field Orientation," Am. J. Roentgenol, 1996, vol. 166(6), pp. 1337-1345.
Moche et al., "Navigation Concepts for MR Image-Guided Interventions," Journal of Magnetic Resonance Imaging, 2008, vol. 27(2), pp. 276-291.
Moche et al., "MRI-Guided Procedures in Various Regions of the Body Using a Robotic Assistance System in a Closed-Bore Scanner: Preliminary Clinical Experience and Limitations," Journal of Magnetic Resonance Imaging, 2010, vol. 31(4), pp. 964-974.
Morrison et al., "MRI-Guided Cryotherapy," Journal of Magnetic Resonance Imaging, 2008, vol. 27(2), pp. 410-420.
Nour et al., "Percutaneous Biopsy from Blinded to MR Guided: An Update on Current Techniques and Applications," Magn. Reson. Imaging Clin. N. Am., 2005, vol. 13(3), pp. 441-464.
Silverman et al., "Interactive MR-guided Biopsy in an Open-Configuration MR Imaging System," Radiology, 1995, vol. 197(1), pp. 175-181.
Stattaus et al., "MR-Guided Core Biopsy With MR Fluoroscopy Using a Short, Wide-Bore 1.5-Tesla Scanner: Feasibility and Initial Results," Journal of Magnetic Resonance Imaging, 2008, vol. 27(5), pp. 1181-1187.
Stattaus et al., "MR-guided liver biopsy within a short, wide-bore 1.5 Tesla MR system," Eur. Radiol., 2008, vol. 18 (12), pp. 2865-2873.
Streitparth et al., "Image-guided spinal injection procedures in open high-field MRI with vertical field orientation: feasibility and technical features," Eur. Radiol., 2010, vol. 20(2), pp. 395-403.
Tatli et al., "Interventional MRI for Oncologic Applications," Tech. Vasc. Interv. Radiol., 2007, vol. 10(2), pp. 159-170.
Terraz et al., "Radiofrequency ablation of small liver malignancies under magnetic resonance guidance: progress in targeting and preliminary observations with temperature monitoring," Eur. Radiol., 2010, vol. 20(4), pp. 886-897.
Wacker et al., "An Augmented Reality System for MR Image-guided Needle Biopsy: Initial Results in a Swine Model," Radiology, 2006, vol. 238(2), pp. 497-504.
Weiss et al., "MR-Guided Biopsy: A Review of Current Techniques and Applications," Journal of Magnetic Resonance Imaging, 2008, vol. 27(2), pp. 311-325.

* cited by examiner

METHOD AND MAGNETIC RESONANCE SYSTEM TO AUTOMATICALLY DETERMINE IMAGING PLANES

BACKGROUND OF THE INVENTION

1. Field of the Invention

The invention concerns a method for automatic determination of imaging planes for an imaging procedure for visualization of a percutaneous intervention of an examination subject. The invention furthermore concerns a method for visualization in the percutaneous intervention, and a magnetic resonance system operable according to such a method.

2. Description of the Prior Art

Percutaneous intervention is a medical technique for minimally-invasive treatment of a patient (examined person). An increasing number of percutaneous interventions are implemented with accompaniment by imaging methods, for instance computed tomography (CT) or magnetic resonance tomography (MRT). Such imaging methods can be used for verification, warning or guidance of the percutaneous intervention. Medical fields in which percutaneous intervention is applied include aspiration biopsy, general biopsy, sclerotherapy, targeted supply of medicines, and heat ablation.

When such medical applications or additional medical applications are supported by imaging methods (for instance CT or MRT), the free-hand manual definition of the imaging planes—i.e. those planes for which the imaging method cyclically provides a visualization of the percutaneous intervention in the form of an image—represents the least complex technique. The correct and optimized alignment of the imaging planes, however, is one of the most essential requirements. It can be useful to continuously visualize the entire needle, the target point, and surrounding structures (for instance sensitive organs). For a manual alignment of the imaging planes, it can be necessary to verify the alignment of the imaging planes during the implementation of the percutaneous intervention. Verification can involve checking the alignment of the imaging planes with regard to general medical considerations, as well as a check with regard to the considerations that are specifically relevant to the technique of the underlying imaging method. For example, a medical professional can have particular requirements for the alignment of the imaging, while an MRT technician attends to other necessities. This can require a high degree of attention for the verification, and therefore make the percutaneous intervention more difficult and error-prone.

Both specialists in the imaging method (for instance MRT technicians or CT technicians) and expert medical personnel can typically participate in the implementation of a percutaneous intervention. Coordination of these parties during the procedure may be poor, or possible only to a limited extent. For example, the operating environment can limit communication and coordination due to a high noise volume. Furthermore, time pressure during the percutaneous intervention can limit a detailed coordination.

Furthermore, the manual arrangement of the imaging planes can be further hindered for special trajectories along which the needle is introduced into an examined person during the percutaneous intervention. Such special trajectories pertain to cases in which the trajectory does not run parallel or is not essentially parallel to one of the anatomical planes (thus for example the coronal, sagittal or transversal plane) of the examined person. Such imaging planes are known as "double oblique trajectories" in the technical terminology. It can be desirable to obtain a well-defined arrangement of the imaging planes relative to the anatomical planes of the examined person; but a different arrangement of the imaging planes (in particular with regard to the instrument trajectory) can enable a better overview and verification during the percutaneous intervention.

For example, it can be desirable for the suitable selection of the imaging planes to enable a verification of the arrangement of the trajectory relative to sensitive structures (organs, for instance). Such organs may be particularly well detectable in imaging planes that align on the conventional anatomical planes of the examined person.

Furthermore, it can be desirable to enable detection of a deviation of the needle used for the percutaneous intervention from the planned trajectory, by a suitable arrangement of the imaging planes.

SUMMARY OF THE INVENTION

Therefore, there is a need to provide an improved method for automatic determination of imaging planes of an imaging method for visualization of a percutaneous intervention. Furthermore, a need exists to provide an improved magnetic resonance system by means of which a method for visualization in a percutaneous intervention can be implemented based on the automatically determined imaging planes. In particular, a need exists for techniques which allow the imaging planes to be determined based on the trajectory, as well as based on well-defined reference planes.

The method and system according to the invention are designed to meet those needs.

In the method according to the invention for automatic determination of imaging planes for an imaging procedure for visualization of a percutaneous intervention of an examined person along an instrument trajectory to a target point, data of a reference coordinate system are acquired that describe three orthogonal reference planes defining the reference coordinate system. Furthermore, the method includes the acquisition of data of the trajectory, that describe the spatial arrangement and the target point of the trajectory, wherein the trajectory has a defined spatial arrangement relative to the reference planes. Furthermore, the method includes the determination of one of these reference planes as a selected reference plane based on the relative arrangement of the reference planes at the trajectory. Furthermore, the method includes the determination of a first imaging plane such that the trajectory lies in the first imaging plane, and such that the first imaging plane has a defined arrangement relative to the selected reference plane. Furthermore, the method includes the determination of a second imaging plane such that the trajectory lies in the second imaging plane, and such that the second imaging plane is orthogonal to the first imaging plane. Furthermore, the method includes the determination of a third imaging plane such that this is orthogonal to the first imaging plane and that is orthogonal to the second imaging plane and includes the target point of the trajectory.

For example, the imaging method can be a modality such as magnetic resonance tomography (MRT) or computed tomography (CT). With such imaging modalities, techniques are known to those skilled in the art that enable MR data or CT data to be detected or acquired from corresponding MR planes or CT planes.

For example, it is possible to obtain the data of the trajectory from a volume data set of the examined person. The volume data set can then include the trajectory, and both the volume data set and the trajectory can have a defined arrangement relative to the reference planes (and therefore to the reference coordinate system). For example, the volume data set can designate data that were acquired with a three-dimensional (3D) imaging method, for instance 3D magnetic resonance imaging. It is also possible for the volume data set to designate a number of two-dimensional slice images that were acquired with a 2D imaging method such as 2D CT or 2D MRT, for instance. The slice images can then have a defined arrangement relative to one another, for instance adjoin one another. It can even be the case that volume data set merely designates a 2D data set imaging a plane along which the trajectory is determined.

It is also possible (for example) to obtain the data of the trajectory in a different way. For example, the data of the trajectory can be obtained based on a position of a needle that can be used for percutaneous intervention.

For example, if the determination of the trajectory is implemented promptly before the percutaneous intervention—for example without moving the examined person between planning and intervention—this can have several advantages with regard to movement artifacts etc., for example. Under some circumstances, however, it may be useful to implement planning of the intervention and the intervention itself in multiple separate process steps. If the needle is used in order to obtain the data of the trajectory, however, a temporal connection can also exist between the percutaneous intervention and the determination of the imaging planes.

The volume data set used to plan (for example) the trajectory in a suitable manner can be obtained from a corresponding imaging method. In general, however, it is not necessary for the imaging method for which the imaging planes are determined according to the invention to be identical to those of the imaging method that supplies the volume data set. There may be different requirements for the initial determination of the trajectory from the volume data set, and the subsequent visualization of the percutaneous intervention using the imaging planes. An image registration or a corresponding coordinate transformation may be necessary in order to obtain a defined arrangement of the volume data set or the trajectory relative to the reference coordinate system or the reference planes.

The reference planes can be suitable to enable an alignment and orientation of the imaging planes that are advantageous with regard to medical aspects. For example, the reference planes can ensure particularly simple or comprehensive alignment and orientation with regard to a sensitive organ, or with regard to specifications by medical personnel, or with regard to the percutaneous intervention. It should be understood that, due to the numerous different types of medical applications, the most varied reference planes are conceivable for a reference coordinate system aligned on the examined person, which is known as a patient coordinate system. In each case, it can be possible to obtain a clear association between the imaging planes and the reference planes by determination of the first imaging plane directly depending on the reference planes, and of the second and third imaging planes implicitly depending on the reference planes. In such a case, it is possible to obtain an improved visualization of the percutaneous intervention based on the imaging planes simultaneously with a simplified arrangement by association with the reference planes, and therefore (for instance) with anatomical reference points of the reference coordinate system.

For example, the trajectory then lies in the first imaging plane when a normal vector of the first imaging plane has no parallel component relative to a vector aligned parallel to the trajectory, and furthermore when no parallel offset is present between the imaging plane and the trajectory. In other words: the first imaging plane can completely include the trajectory.

An increased overview, and improved visualization of the percutaneous intervention along the trajectory, can be achieved by such an arrangement of the first and second imaging planes, as well as furthermore by the orthogonal or perpendicular arrangement of the first and second imaging planes relative to one another.

For example, it can furthermore be possible that a normal vector of the third imaging plane has only one parallel component (i.e. no perpendicular component) relative to a vector describing the trajectory. Because the third imaging plane is orthogonal or perpendicular to the first and second imaging plane, and because the third imaging plane includes the target point of the trajectory, the attainment (reaching) of the target point by a needle used for percutaneous intervention can be visualized by means of the third imaging plane. It can also be possible to take into account surrounding, possibly sensitive structures (for instance organs) in the visualization of the percutaneous intervention.

In particular, the reference planes can be anatomical planes of the examined person. For example, the reference planes can be the transverse or axial plane, the sagittal plane, and the frontal or coronal plane of the examined person. The transverse plane, the sagittal plane and the frontal plane can respectively be anatomical planes of the examined person that are arranged relative to the target point of the trajectory, or can also be anatomical planes arranged relative to a middle point of the body of the examined person, for example—i.e. pertain to the planes known as median planes.

For example, if the transverse plane, the sagittal plane and the frontal plane are used as reference planes, this can have the effect of the imaging planes being aligned such so as to be close to these conventional anatomical planes of the examined person. For example, these imaging planes may be essentially parallel to and/or make only a small angle with respect to, and/or have a small separation from the conventional anatomical planes. In such a case, the visualization of the percutaneous intervention can be improved both with regard to verification of the intervention and with regard to alignment relative to the main anatomical slice planes of the examined person.

In this context, the determination of the first imaging plane can be implemented such that a plane normal of the first imaging plane is parallel to a component of the plane normal of the selected reference plane that is perpendicular to the trajectory. For example, the plane normal of the selected reference plane can be decomposed into components respectively perpendicular and parallel to the trajectory. The plane normal of the imaging plane can then be parallel to those of these decomposed components of the reference plane normal that are perpendicular to the trajectory. Due to a minimized clearance (for instance a minimized angle) between the trajectory and the selected reference plane, the component of the plane normal of the reference plane perpendicular to the trajectory can typically be significantly larger (for instance by a factor of 1.5, or a factor of 2, or a factor of 10 or more) than the component parallel to the trajectory of the normal of the reference plane. In other words, this can enable the imaging planes to be aligned optimally close to the reference planes or, respectively, the anatomical planes of the examined person.

The determination of the first imaging plane can accordingly occur such that it has a minimized clearance with the selected reference plane. For example, the imaging plane can be determined in an iterative minimization of a clearance (for example an angle) with respect to the selected reference plane. The alignment with the minimum clearance can be chosen, or can be an alignment with a fixed relation to the minimum clearance. The clearance can be calculated based on the angle between the first imaging plane and the selected reference plane. For example, the first imaging plane can be arranged by minimization of this angle.

The first imaging plane can be arbitrarily rotated further around the trajectory based on the sole criterion that the trajectory lies in this imaging plane. However, a specific orientation with regard to the trajectory and the selected reference plane can be selected by minimization of the clearance (for example of the angle).

In such a case, the vectors $\vec{V}_{1,1}$ and $\vec{V}_{1,2}$ spanning the first imaging plane can be described with regard to a $\vec{d}_p$ describing the trajectory, as well as the normal vector of the selected reference plane $\vec{n}_i n_i$, can be described by the following dependencies:

$$\vec{V}_{1,1} = \vec{d}_p \quad (1),$$

$$\vec{V}_{1,2} = \vec{n}_i \times \vec{d}_p \quad (2).$$

The vectors spanning the first imaging plane are thus on the one hand parallel to the trajectory (see Equation 1) and on the other hand parallel to a cross product of the trajectory and the plane normal of the reference plane (see Equation 2).

It should be understood that, for the case that the first imaging plane is determined by means of Equations 1 and 2, a corresponding clearance with the selected reference plane can also simultaneously be minimal.

The vectors $\vec{V}_{2,1}$ and $\vec{V}_{2,2}$ spanning the second imaging plane can accordingly be described by the following Equations:

$$\vec{V}_{2,1} = \vec{d}_p \quad (3),$$

$$\vec{V}_{2,2} = \vec{V}_{1,2} \times \vec{d}_p \quad (4).$$

The vectors $\vec{V}_{3,1}$ and $\vec{V}_{3,2}$ spanning the third imaging plane can accordingly be described by the following Equations:

$$\vec{V}_{3,1} = \vec{V}_{1,1} \times \vec{V}_{1,2} \quad (5),$$

$$\vec{V}_{3,2} = \vec{V}_{1,2} \times \vec{V}_{2,2} \quad (6).$$

Furthermore, the method can include the calculation of a clearance for at least two of the reference planes relative to the trajectory, wherein the determination of the selected reference plane takes place based on the calculated clearance. For example, the clearance can be calculated for all reference planes. For example, those planes among the reference planes that have a minimum or maximum clearance can be chosen as the selected reference plane. In such a case, it can be possible that the imaging planes are aligned optimally close to the reference planes, for example anatomical planes of the examined person. However, it can also be possible to exclude specific reference planes in advance of the determination of the clearance, and thus to prevent that such specific reference planes are selected. For example, this can have medical grounds or can occur based on a preference of operating personnel, for instance.

Furthermore, it can be possible for the data of the reference coordinate system to include a lateral orientation of the reference planes, wherein the determination of at least one of the imaging planes takes place so that its lateral orientation is based on the lateral orientation of one of the reference planes for which a clearance is minimal relative to the at least one imaging plane.

In general, a plane can have no orientation or preferential direction outside of the normal direction. This means that a plane has no preferential direction or orientation within the plane. However, a lateral orientation—meaning an orientation within the plane—can enable an image which is acquired with the imaging method for the respective imaging plane to align corresponding to the lateral orientation. For example, a mirror-inverted or upside-down acquisition or reproduction of the image can thus be prevented. Subjects arranged to the left or right side are correspondingly shown in the image. This can allow the orientation in the visualization of the percutaneous intervention to be improved.

For example, a lateral orientation can be enabled by providing a preferential direction in the data of the reference coordinate system. A lateral orientation of the reference planes can also take place through the description of the reference planes by means of row, column and normal vectors—known as r-, c-, n-vectors—that are defined relative to the reference coordinate system. The components that respectively relate to the row or column vectors can then imply a defined lateral orientation. Since the alignment of the imaging planes is determined based on the reference planes, it can then be possible to determine the lateral orientation of the imaging planes based on the lateral orientation of the associated reference plane.

In general, the lateral orientation of one of the imaging planes can be determined to be identical to the lateral orientation of the respectively associated reference plane, or different by a well-defined magnitude.

Furthermore, in this regard the method can include the alignment, by means of a coordinate rotation, of the lateral orientation of the at least one imaging plane on the lateral orientation of the reference plane for which the clearance is minimal relative to the at least one imaging plane. The alignment by means of coordinate transformation can be implemented for the corresponding imaging plane, depending on for which of the first, second and third imaging planes a determination of the lateral orientation takes place based on the lateral orientation of the respective associated reference plane. In general, it is possible that all imaging planes are determined with corresponding orientation.

The clearance can be calculated based on an angle between the trajectory and the appertaining plane, or based on an angle between the appertaining planes. For example, the calculation of the clearance for one of the reference planes relative to the trajectory can include the calculation of the angle between the reference plane and the trajectory. The calculation of the clearance between an imaging plane and a reference plane can accordingly include the calculation of the angle between the imaging plane and the reference plane. For example, if the angle between a plane and the trajectory or, respectively, between two planes is small, the clearance can also assume a small value. Various methods to calculate a clearance between planes and vectors or, respectively, between planes which can be used equivalently are known to those skilled in the art.

Furthermore, the method can include obtaining a reference point of the volume data set, wherein the determination of at least one of the imaging planes takes place so that its center is aligned on the reference point. The volume data set can include the trajectory.

For example, the reference point of the volume data set can designate the geometric center of the volume data set. It is also possible that the reference point designates a characteristic location with regard to the imaging method, for instance the isocenter of a magnetic resonance system etc.

The imaging planes can have a laterally limited extent, i.e. a limited extent in the plane. This can be the case since the imaging method incurs technical limitations of the maximum image size of an image acquired for an imaging plane. For example, a normal through a center of one of the imaging planes can include the reference point.

An alignment of the center of the imaging planes on the reference point can then have the effect that the imaging planes are centered relative to the volume data set or are arranged well-defined relative to the center of the volume data set. Since the volume data set includes the trajectory, this can have the effect that the imaging planes cover a region which is particularly suitable for visualization of the percutaneous intervention relative to the trajectory.

For example, in the case of MRT the field of view can be limited to a diameter of approximately 50 cm relative to a central axis that proceeds through the center of the magnetic resonance data acquisition unit (scanner). In particular, limitations can exist in the radial direction relative to the central axis. It can then be desirable for the imaging planes to be determined within the field of view. An alignment or centering on the reference point of the volume data set can then enable it to ensure that the trajectory is sufficiently imaged for visualization of the percutaneous intervention.

In this regard, the determination of the third imaging plane can occur such that the center of the third imaging plane is aligned on the target point of the trajectory. For example, this can be useful for the visualization of the imaging method based on the third imaging plane to centrally depict the target point of the trajectory in the correspondingly acquired image. It may be possible for the center of the third imaging plane to be coincident with the target point of the trajectory.

It is also possible for the third imaging plane, as explained above, to be aligned based on the reference point of the volume data set.

Furthermore, in this regard the method can include the alignment (by means of a linear coordinate shift) of the center of at least one of the imaging planes on the reference point or the target point of the trajectory. The specific presentation and implementation of the coordinate shift can be dependent on the mathematical formalism that is used. Suitable techniques are known to those skilled in the art.

For the case that the different planes will represent r-, c-, n-vectors in the mathematical formalism of the rows, columns and normal vectors, the coordinate shift can be expressed as follows:

$$\vec{g}_{new} = \vec{g} + \mu \vec{r} + \xi \vec{c} \quad (7),$$

$$\mu = (\vec{g} - \vec{g}_0)^T \cdot \vec{r} \quad (7a),$$

$$\xi = (\vec{g} - \vec{g}_1)^T \cdot \vec{c} \quad (7b).$$

wherein $\vec{g}_{new}$ designates the new center of an imaging plane, and $\mu$ designates a displacement along the r-vector and $\xi$ designates a shift along the c-vector. $g_0$ designates the reference point, and g designates the old center of the imaging plane.

Through the implementation of such a coordinate shift, it can be possible to ensure that the center of the imaging plane is well-defined relative to the trajectory, the reference planes, and the field of view of the imaging method. This can enable an improved visualization of the percutaneous intervention to be achieved.

Furthermore, the correct alignment of the planes can reduce image defects known as anti-aliasing artifacts, in particular with regard to an embodiment of the invention in which the imaging method uses an MRT technique. Such artifacts can occur particularly in the use of undersampling schemes, which undersample the spatial frequency domain and reconstruct the missing information, for example by use of multiple coils. The corresponding effects can be considered as an effect of the Fourier transformation from positional frequency space into positional space. Corresponding MR acquisition sequences would be "SMASH", "SENSE", "GRAPPA" as they are known to those skilled in the art.

In a further embodiment, the invention concerns a method for visualization of a percutaneous intervention of an examined person along a trajectory to a target point. The method includes the timed acquisition of magnetic resonance data for magnetic resonance planes, wherein the magnetic resonance planes are determined with the method for automatic determination of imaging planes according to the above aspect. The method furthermore includes the visualization of the magnetic resonance (MR) data as two-dimensional real-time images of the MR planes.

The use of MRT as an imaging method for visualization of the percutaneous intervention can have the effect that a particularly flexible imaging can take place with regard to the imaging planes or, respectively, MR planes. In MRT it is possible to achieve an imaging along arbitrarily oriented imaging planes or MR planes by suitable linear superposition of orthogonally oriented gradient fields that are used for spatial coding in an MR system.

Furthermore, the use of MRT as an imaging method for visualization of percutaneous intervention can have the effect that an increased contrast is achieved for soft tissue parts (in particular organs). This can enable an improved monitoring during the percutaneous intervention to avoid damaging sensitive structures (for instance organs) that are located closely adjoining the trajectory).

Furthermore, the method for visualization of the percutaneous intervention according to this embodiment of the invention can include the timed acquisition of magnetic resonance data with a clock rate which detects subsequently acquired magnetic resonance data of different magnetic resonance planes with a time offset that is smaller than a longitudinal relaxation time of the nuclear magnetization. For example, the nuclear magnetization can concern protons (1-H) or nitrogen nuclei (14-N), or other suitable nuclei. Corresponding longitudinal relaxation times are known to those skilled in the art and typically lie in the range of a few milliseconds to seconds.

This can have the effect that the trajectory has an improved visibility due to saturation artifacts. In particular if the MR planes were determined by means of a method for automatic determination of imaging planes according to a previously discussed aspect of the present invention, the first MR plane and the second MR plane can have an intersection set of imaging pixels which are arranged along the trajectory. If the acquisition of MR data takes place so quickly that (for example) the MR data are acquired from the second MR plane before the nuclear spins have relaxed back into a steady state parallel to a longitudinal direction (for example parallel to a basic magnetic field of an MR system) following the acquisition of the MR data from the first MR plane, the MR data from the second MR plane have a relaxation artifact at the point of the trajectory. For example, the MR data of the second MR plane there can have a reduced contrast relative to the surrounding MR data and appear somewhat darker. Such a relaxation artifact can be used to enable an improved visualization of the trajectory during the percutaneous intervention, and therefore to detect deviations of the needle from the planned trajectory early during the insertion, for instance. The utilization of such a relaxation artifact can be particularly advantageous in the case of an arrangement of the MR planes as described above.

The method for visualization of a percutaneous intervention can furthermore include the automatic monitoring of the incidence of events that are selected from the group that includes the following elements: signal deviation of the MR data of the third magnetic resonance plane; sensitive subject on the trajectory in the acquired MR data of the first and/or second MR plane; susceptibility artifact on the trajectory in the acquired MR data of the first and/or second MR plane.

For example, a signal deviation of the MR data from the third MR plane can be assessed as an indicator that the needle of the percutaneous intervention has reached the target point of the trajectory. This signal deviation can pertain to a susceptibility artifact caused by the needle.

A susceptibility artifact on the trajectory of the acquired MR data of the first and/or second MR plane can be assessed in turn as an indicator of the presence of the needle at the appertaining point. With suitable embodiments of the needle, the needle can be given a static (DC) susceptibility that deviates from the DC susceptibility of the environment. For example, the DC susceptibility of the environment can assume values of water or tissue. Such values are known to those skilled in the art. In and around the region of the needle, a basic magnetic field which is used for MRT can then have a value that is varied relative to the surrounding tissue due to a phenomenon known as the susceptibility mismatch. This can affect the imaging in the appertaining domain. For example, a shift of spatial points or an altered contrast can be achieved since, for instance, the resonant frequencies of k-spaces have a spatial dependency. This can produce an improved visualization of the position of the needles in the percutaneous intervention.

According to a further aspect, the invention concerns a magnetic resonance system for visualization of a trajectory for percutaneous intervention. The magnetic resonance system has a computer that is configured to implement the following steps. Data of a reference coordinate system are obtained that describe three orthogonal reference planes defining the reference coordinate system. Data of the trajectory are also obtained, that describe an arrangement and the target point of the trajectory, the trajectory having a defined arrangement in relation to the reference planes. One of these reference planes is determined as a selected reference plane based on the arrangements of the reference planes relative to the trajectory. A first magnetic resonance plane is determined such that this trajectory lies in the first magnetic resonance plane, and such that this first magnetic resonance plane has a specific arrangement relative to the selected reference plane. A second magnetic resonance plane is determined such that the trajectory lies in this second magnetic resonance plane, and such that this second magnetic resonance plane is orthogonal to the first magnetic resonance plane. A third magnetic resonance plane is determined such that it is orthogonal to the first magnetic resonance plane, and is orthogonal to the second magnetic resonance plane, and includes the target point.

Furthermore, the magnetic resonance system can include an imaging unit that is configured to implement the following steps: timed acquisition of magnetic resonance data for the magnetic resonance planes, and visualization of the magnetic resonance data as two-dimensional real-time images of the magnetic resonance planes.

With such a magnetic resonance system according to the invention, advantages are achieved that correspond to those described above with the method to automatically determine imaging planes according to the invention, and the method to visualize a percutaneous intervention according to an embodiment of the present invention.

The invention also concerns a computed tomography apparatus designed to provide a visualization of a trajectory for a percutaneous intervention. The computed tomography apparatus has a computer that is configured to implement the following steps. Data of the trajectory are also obtained, that describe an arrangement and the target point of the trajectory, the trajectory having a defined arrangement in relation to the reference planes. One of these reference planes is determined as a selected reference plane based on the arrangements of the reference planes relative to the trajectory. A first computed tomography plane is determined such that this trajectory lies in the first computed tomography plane, and such that this first computed tomography plane has a specific arrangement relative to the selected reference plane. A second computed tomography plane is determined such that the trajectory lies in this second computed tomography plane, and such that this second computed tomography plane is orthogonal to the first computed tomography plane. A third computed tomography plane is determined such that it is orthogonal to the first computed tomography plane, and is orthogonal to the second computed tomography plane, and includes the target point.

The features of the previously described embodiments and aspects of the invention can be combined with one another. The features can be used not only in the described combinations but also in other combinations without deporting from the scope of the invention. For example, it is possible to use the method to automatically determine imaging planes of an imaging method relative to the automatic determination of magnetic resonance planes or computer tomography planes. According to a further aspect, the invention also concerns a computed tomography system that can be used to implement the method to automatically determine imaging planes of a computed tomography method and the method to visualize a percutaneous intervention according to aspects and embodiments of the invention that are discussed above.

DESCRIPTION OF THE PREFERRED EMBODIMENTS

In the following, techniques to determine imaging planes that can be used for an imaging method to visualize a percutaneous intervention, and techniques to visualize the percutaneous intervention itself, are discussed in detail with reference to the figures. In the figures, reference is made to techniques of magnetic resonance tomography (MRT), but it should be understood that corresponding techniques can also be applied to other imaging methods, for instance computed tomography (CT). The figures accordingly should not be construed as limiting with regard to applicability to MRT, but rather merely illustrate the basic techniques and concepts.

Figure 1:
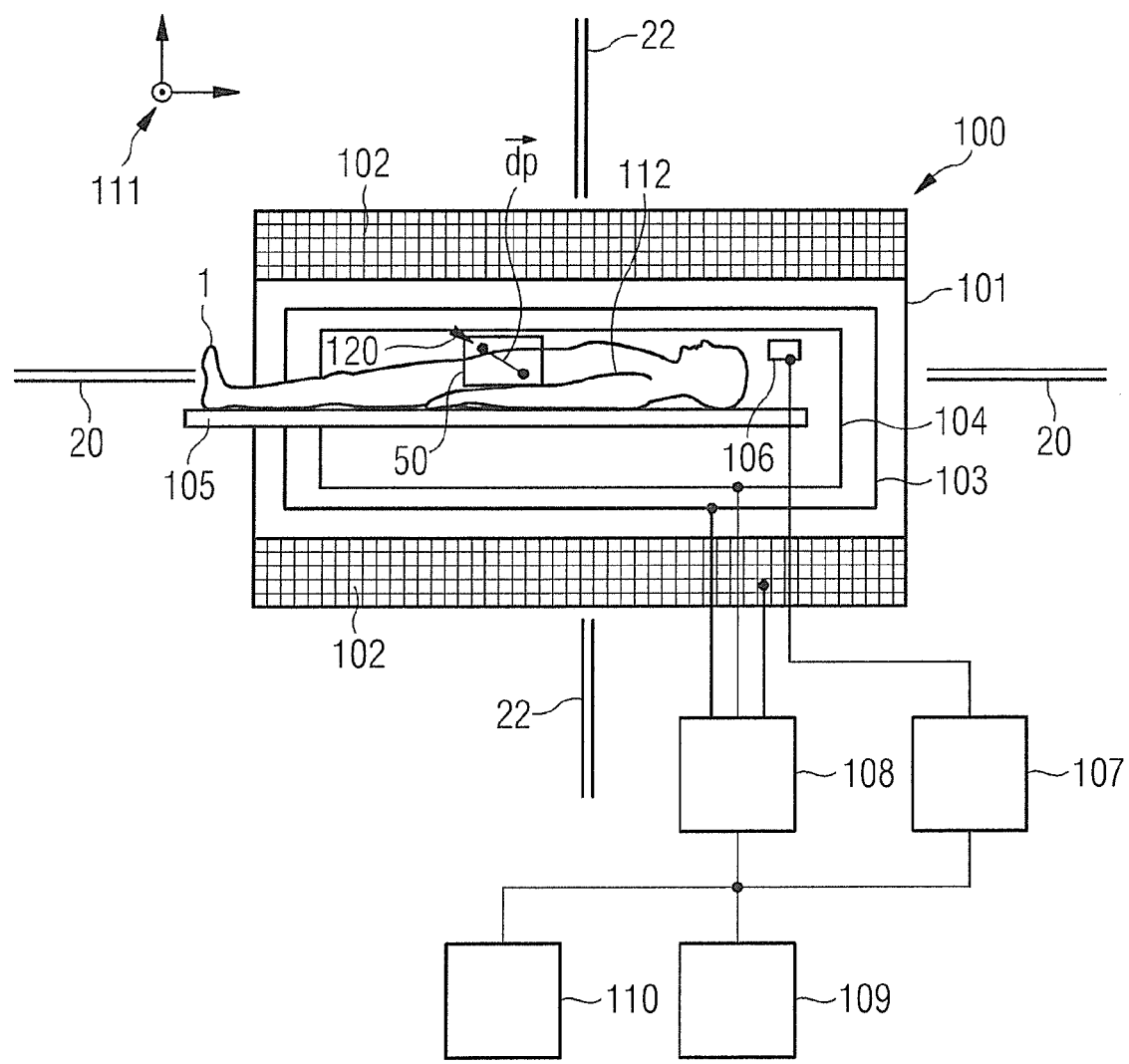
FIG. 1 schematically illustrates a magnetic resonance system that can be operated to implement a method according to the invention to automatically determine imaging planes and a method according to the invention to visualize a percutaneous intervention of an examined person.

A magnetic resonance (MR) system 100 is shown in FIG. 1. An examined person 1 is placed on a table or, respectively, a bed 105. The examined person 1 is located with a tube 101 defined by a basic field magnet 102. Although the MR system 100 of FIG. 1 is represented in a closed embodiment characterized by the tube 101, it should be understood that corresponding techniques can also be used with regard to open MR systems. Suitable embodiments of MR systems are known to those skilled in the art. In particular, open MR systems can have advantages with regard to the implementation capability of a percutaneous intervention given simultaneous imaging. Namely, the accessibility to locations along the examined person 1 can in particular be improved in open MR systems.

Such a percutaneous intervention at the examined person 1 is schematically illustrated in FIG. 1 by the trajectory $\vec{d}_p$. A needle 120 can be introduced along the trajectory $\vec{d}_p$. The MR system 100 can be used to visualize this percutaneous intervention. In particular, a monitoring or verification of the supply of the needle 120 can take place along the trajectory $\vec{d}_p$. Such a monitoring of the percutaneous intervention requires a defined association of the alignment of the trajectory $\vec{d}_p$ relative to the coordinate system 111 of the MR system 100, as well as a defining reference coordinate system with regard to anatomical planes of the examined person 1. The coordinate system 111 can also be designated as an apparatus coordinate system.

A coronal anatomical plane 20 and a transversal or, respectively, axial anatomical plane 22 are shown in FIG. 1. A sagittal anatomical plane 21 (not shown in FIG. 1) lies in the plane of the drawing.

In order to achieve a visualization of the percutaneous intervention with improved clarity and simple alignment and orientation relative to the examined person 1 and relative to the trajectory $\vec{d}_p$ in images generated by the MR system 100, techniques according to the invention can be used as described in the following.

To acquire MR data, the MR system 100 has an imaging unit 108 connected with a gradient system 103 and a radio-frequency coil system 104. Furthermore, the imaging unit 108 is connected with the basic field magnet 102. An acquisition of MR data along arbitrarily oriented MR planes with MR acquisition sequences can take place by means of suitable control of these components 102, 103, 104. In particular, a linear superposition of spatially coded gradient fields that are generated by means of the gradient system 103 can enable an arbitrary orientation of the MR planes.

The MR system can be controlled by a human/machine interface 110. Acquired MR data can be output as MR images on a monitor 109.

The MR system 100 can have a field of view which extends within the tube. Within the field of view, MR data can have a high quality, for example low spatial distortion and low signal noise. For example, the field of view can extend approximately 25 cm in all directions in the radial direction from a central axis of the tube 101. An isocenter 112 of the MR system—placed in the center of the tube 101, for example—can describe an axial arrangement of the field of view. For example, the field of view can have an extent of multiple 10's of cm—100 cm, for instance—in the axial direction relative to the isocenter 112.

Furthermore, the MR system 100 has a computer 107 connected with a positioning system, for instance a laser positioning system 106. The system 106 can be used for registration of the examined person 1 in the MR system 100, meaning that the system 106 can be used to determine the relative alignment of the anatomical planes 20, 21, 22 relative to the coordinate system 111 of the MR system 100.

For example, it is then possible to acquire a volume data set 50 of MR data by means of the imaging unit 108, which volume data set 50 is arranged such that it includes the trajectory $\vec{d}_p$. A precise planning of the trajectory $\vec{d}_p$ can take place using the volume data set 50. If the volume data set 50 is acquired with the MR system 100, it must essentially be placed within the field of view of the MR system 100. It is also possible for the volume data set 50 to already have been acquired at an earlier point in time and has a known alignment relative to the planes 20, 21, 22. A relative positioning can then be made via the registration with system 106.

In general, with these techniques it is possible to set the alignment of the trajectory $\vec{d}_p$ relative to the anatomical planes 20, 21, 22, and relative to the coordinate system 111 of the MR system 100.

Although the units and systems in FIG. 1 are presented as separate units, it is generally possible that different units are combined into one unit. It is possible to implement different units as software, hardware or a combination thereof.

Figure 2:
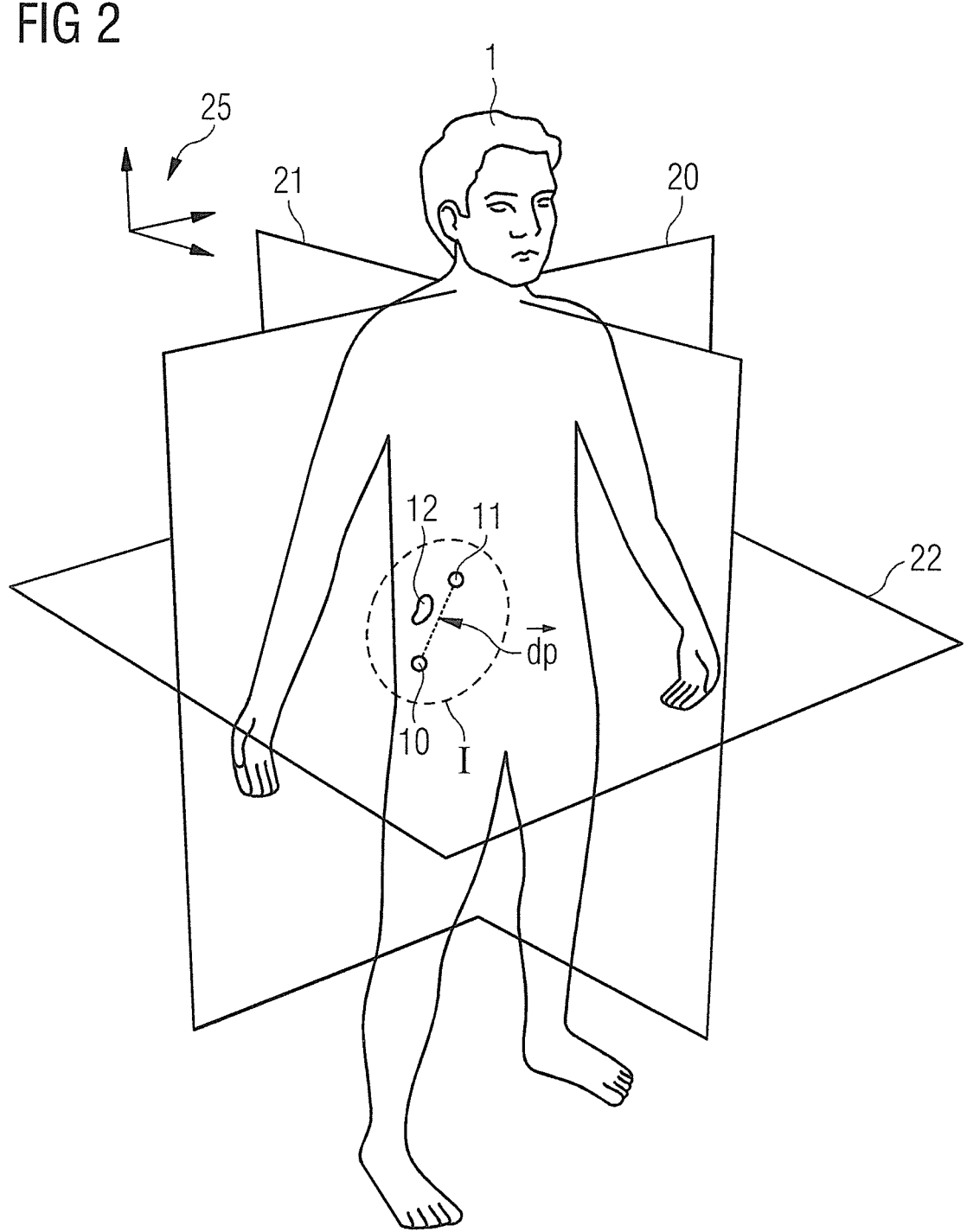
FIG. 2 schematically illustrates anatomical planes of an examined person, and in particular their arrangement relative to a trajectory of a percutaneous intervention.

FIG. 2 illustrates the connection of the arrangement of the trajectory $\vec{d}_p$ closer to the anatomical planes 20, 21, 22 of the examined person 1. In FIG. 2, the examined person 1 is shown together with the anatomical planes, namely the coronal plane 20, the sagittal plane 21 and the transversal plane 22. These planes 20, 21, 22 are situated relative to the reference coordinate system 25, which is defined relative to the examined person 1.

The trajectory $\vec{d}_p$ is characterized by a starting point 10 that marks the entrance of the needle 120 into the examined person 1. Furthermore, the trajectory $\vec{d}_p$ is characterized by a target point 11. The target point 11 can be predetermined by medical requirements and depend on the type of medical application. A sensitive subject 12 (for instance an organ or bone) can possibly be located adjacent to the trajectory $\vec{d}_p$. The sensitive subject 12 should not be met by the needle 120 during the insertion of the needle 120 along the trajectory $\vec{d}_p$. The trajectory is a straight line in FIG. 2.

As median planes, the anatomical planes 20, 21, 22 of FIG. 2 are depicted centered on the middle point of the body of the examined person 1. It is also conceivable that the anatomical planes 20, 21, 22 are centered with regard to the points 10, 11, for example, or with regard to a middle point of the trajectory $\vec{d}_p$.

Figure 3:
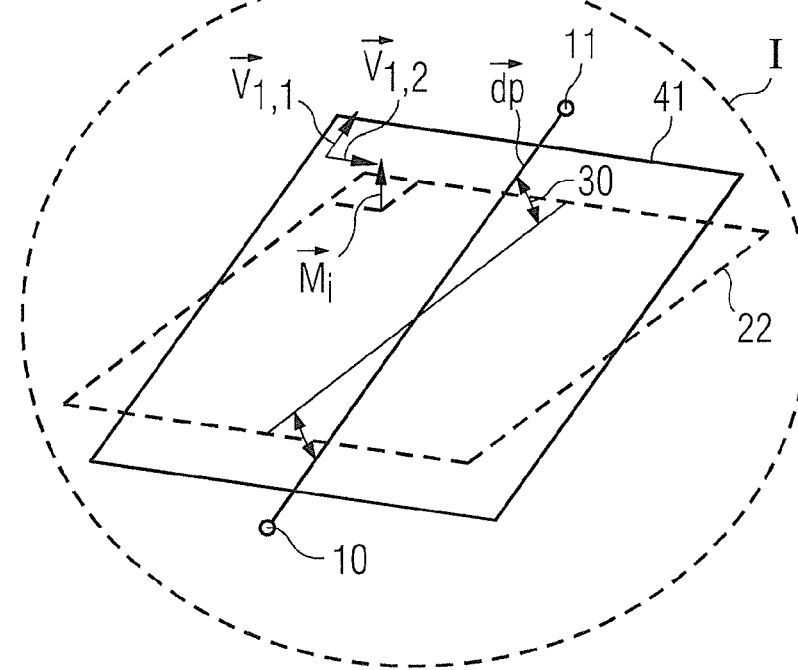
FIG. 3 illustrates the determination of a first imaging plane based on a reference plane and a trajectory along which a percutaneous intervention is planned.

FIG. 3 is an enlargement of the section of FIG. 2 that is marked with I. The determination of a first imaging plane or, respectively, MR plane 41 based on the reference planes 20, 21, 22 and the trajectory $\vec{d}_p$ is explained in detail in FIG. 3. As is clear from FIG. 3, the trajectory $\vec{d}_p$ encloses a small, finite angle 30 with the transverse plane 22 of the examined person 1 (not shown in FIG. 3). The trajectory $\vec{d}_p$ correspondingly encloses other angles with the coronal plane 20 (shown in FIG. 3) and the sagittal plane 21 (shown in FIG. 3). However, the last cited angle is larger than the angle 30 which the trajectory $\vec{d}_p$ encloses with the transverse plane. The computer 107 of MR system 100 is set up in order to calculate these angles and determine a clearance between the trajectory $\vec{d}_p$ and the planes 20, 21, 22 based on the calculated angles.

For example, the clearance can be equal to the value of the angle 30. Since the angle 30 which encloses the trajectory $\vec{d}_p$ with the transverse plane 22 is smaller than the angle of the trajectory $\vec{d}_p$ with the coronal and sagittal plane 20, 21, the transverse plane 22 is selected. Therefore, the first imaging plane 41 is determined relative to the transverse plane 22. The first MR plane 41 is therefore determined such that it includes the trajectory $\vec{d}_p$, and such that its plane normal is parallel to a component of the plane normal (designated with $\vec{d}_p$ in FIG. 3) of the transverse plane 22 as a selected reference plane that is perpendicular to the trajectory $\vec{d}_p$. This has the effect that the first MR plane 41 is optimally close to that anatomical plane 20, 21, 22 of the examined person 1 that encloses the smallest angle with the trajectory $\vec{d}_p$. This means that the first MR plane 41 has an alignment that comes optimally close to the alignment of the nearest anatomical plane 20, 21, 22, and simultaneously includes the trajectory $\vec{d}_p$. From FIG. 3 it is clear that the trajectory $\vec{d}_p$ lies in the first MR plane 41.

Furthermore, from FIG. 3 it is clear that the vectors and $\vec{V}_{1,1}$ and $\vec{V}_{1,2}$ spanning the first MR plane 41 satisfy the following equations with regard to the trajectory $\vec{d}_p$ and the plane normal $\vec{n}_i$ of the transversal plane 23:

$$\vec{V}_{1,1} = \vec{d}_p \quad (1),$$

$$\vec{V}_{1,2} = \vec{n}_i \times \vec{d}_p \quad (2).$$

Figure 4:
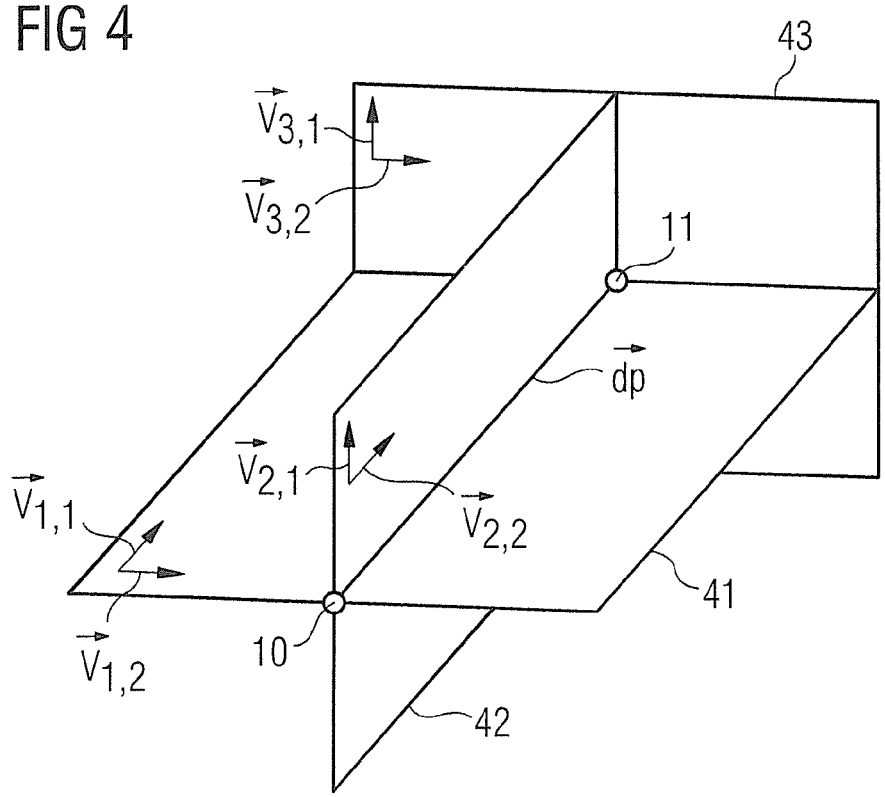
FIG. 4 illustrates the first imaging plane from FIG. 3 and a second and third imaging plane for visualization of a percutaneous intervention along a planned trajectory according to a method according to one aspect of the invention.

The arrangement of a second MR plane 42 and a third MR plane 43 relative to the first MR plane 41 and the trajectory $\vec{d}_p$ is illustrated in detail in FIG. 4. As is clear from FIG. 4, the two first and second MR planes 41, 42 that are perpendicular or orthogonal to one another are arranged along the planned trajectory $\vec{d}_p$ such that this is located at their intersection points. The trajectory $\vec{d}_p$ lies in both the first MR plane 41 and the second MR plane 42. Furthermore, the third MR plane 43 is arranged orthogonal to the first and second MR planes 41, 42 and includes the target point 11 of the trajectory $\vec{d}_p$.

Such an arrangement of the planes 41, 42, 43 allows a check to be made as to whether a sensitive subject 12 (not shown in FIGS. 3 and 4) is encountered along the trajectory $\vec{d}_p$. Furthermore, the arrangement of the planes 41, 42, 43 as it is illustrated in FIG. 4 can have the effect that, given suitable clocking of the acquisition of MR data, saturation bands are generated along the intersection lines between the planes 41, 42, 43 due to incompletely relaxed longitudinal magnetization. Such saturation bands can allow the trajectory $\vec{d}_p$ to be identified in the MR data that are acquired for the planes 41, 42, 43 or, respectively, can allow the target point 11 to be represented. For example, saturation bands can produce a reduced contrast in MR images based on the MR data. An improved orientation and placement of the needle 120 during the percutaneous intervention can be possible on the basis of these saturation bands. Furthermore, it is possible to detect that the needle 120 has reached the target point 11. For example, such a detection can take place based on a monitoring of the changes of the MR data acquired for the third MR plane 43. If a cross section needle artifact—for instance a susceptibility artifact—appears in the third MR plane 43, this can be assessed as an indicator of the successful placement of the needle 120.

The vectors $\vec{V}_{2,1}$ and $\vec{V}_{2,2}$ are those vectors which span the second MR plane 41. Correspondingly, the vectors $\vec{V}_{3,1}$ and $\vec{V}_{3,2}$ are those vectors which span the third MR plane 43. As is apparent from FIG. 4, these vectors satisfy the following equations:

$$\vec{V}_{2,1} = \vec{d}_p \quad (3),$$

$$\vec{V}_{2,2} = \vec{V}_{1,2} \times \vec{d}_p \quad (4),$$

$$\vec{V}_{3,1} = \vec{V}_{1,1} \times \vec{V}_{1,2} \quad (5),$$

$$\vec{V}_{3,2} = \vec{V}_{1,2} \times \vec{V}_{2,2} \quad (6).$$

Such equations determine an arrangement of the first, second and third MR planes 41, 42, 43 as was discussed in the preceding with reference to FIGS. 3 and 4.

However, due to technical limitations of the imaging method (here MRT) it can also be necessary or, respectively, desired to determine the MR planes 41, 42, 43 with a lateral extent and/or lateral orientation. For example, it can be possible that the field of view of the MR system 100 limits the maximum lateral extent of the MR planes 41, 42, 43. On the other hand, it can be desired to limit the imaging to an actual region that is relevant to the visualization of the percutaneous intervention. In such a case, it may be necessary to align the center of the MR planes 41, 42, 43 such that the entire relevant region of the percutaneous intervention is visualized in spite of the limited lateral extent of the planes 41, 42, 43. This is discussed in the following with regard to FIG. 5.

Figure 5:
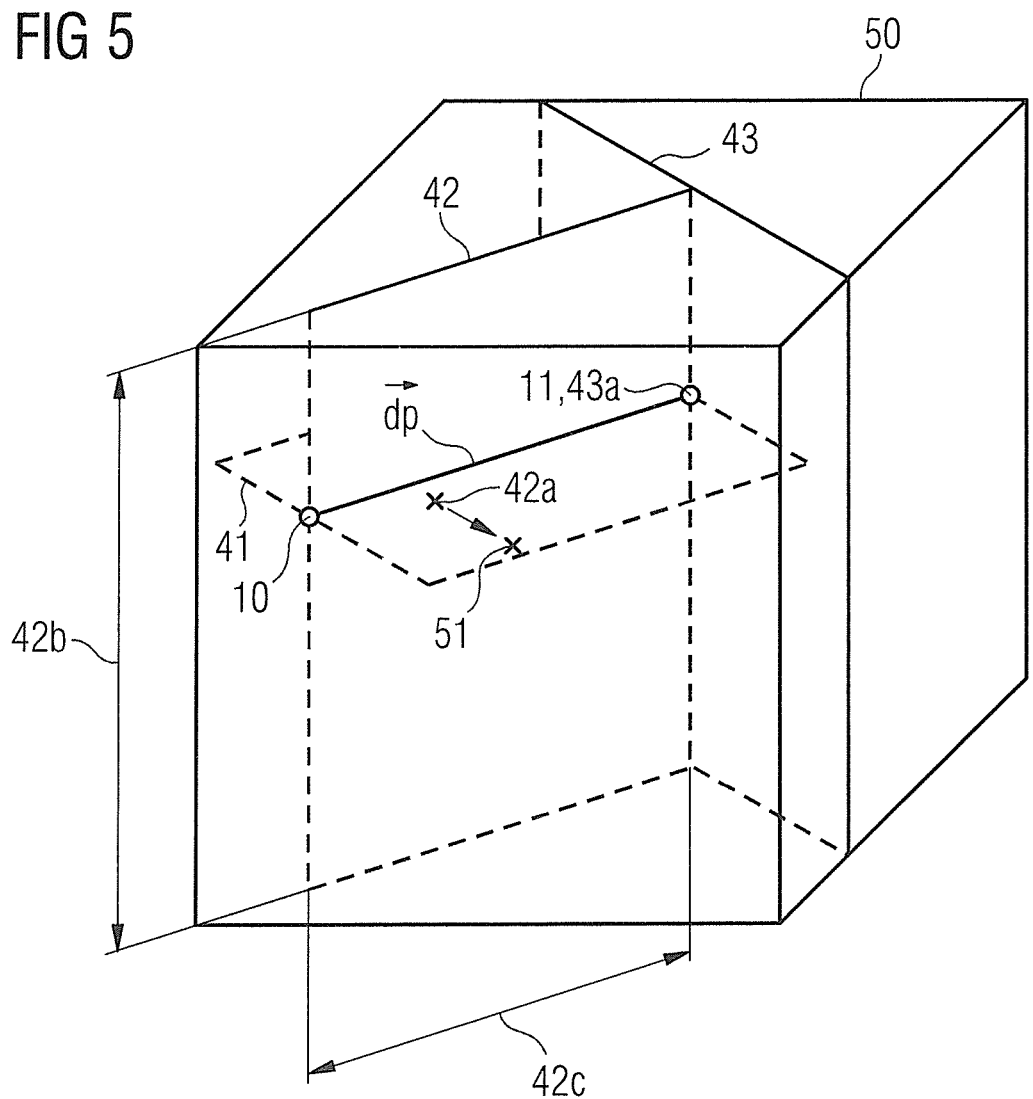
FIG. 5 illustrates the arrangement of the imaging planes from FIG. 4 relative to a volume data set which includes the trajectory of the percutaneous intervention.

In FIG. 5, the volume data set 50 is presented as it has already been discussed with reference to FIG. 1. In the case of FIG. 5, the volume data set 50 has a cubic shape; however, in general it can also have a different shape, for instance it can be spherical. For example, it is possible that the volume data set 50 is acquired immediately after the introduction of the examined person 1 into the MR system 100. Using the volume data set 50 it can then be possible to plan the trajectory $\vec{d}_p$. However, it can also be possible that the volume data set 50 was determined at an earlier point in time and/or with a different imaging method. It can then be necessary to produce an alignment of the volume data set 50 with the coordinate system 111. Various techniques for this are known.

In particular, the volume data set 50 completely includes and comprises the trajectory $\vec{d}_p$. Furthermore, the volume data set 50 is characterized by a reference point 51 which—in the case of the embodiment as it is represented in FIG. 5—designates the center of the volume data set 50. The first and second MR planes 41, 42 are determined in FIG. 5 such that their centers are aligned on the reference point 51. A center 42A of the second MR plane 42 (which center 42A is defined in relation to the lateral extents 42B and 42C of this plane) is illustrated in FIG. 5. For example, the determination of the second MR plane 42 can take place so that a normal vector (illustrated by means of the arrow in FIG. 5) through the center 42A of the second MR plane 42 coincides with the reference point 51 of the volume data set 50 or, respectively, touches or encompasses this. However, it is also possible to use other arrangements of the MR planes 41, 42, 43 relative to the reference point 51 for determination. For example, an offset can be present between a normal through the centers of the MR planes 41, 42, 43 and the reference point 51.

The determination of the third MR plane 43 in FIG. 5 has taken place such that this MR plane 43 has a determined arrangement relative to the target point 11 of the trajectory $\vec{d}_p$. In other words: in one embodiment of the present invention, the arrangement in the third MR plane takes place relative to the target point 11 of the trajectory $\vec{d}_p$, and not relative to the reference point 51 of the volume data set 50. In the case of FIG. 5, a center 43A of the third MR plane 43 is coincident with the target point 11 of the trajectory $\vec{d}_p$. In spite of this, the lateral extent of the third MR plane 43 is limited by the volume data set.

In general, the MR planes 41, 42, 43 can be determined so that—via relative positioning with regard to the volume data set 50—it is ensured that they include the entire trajectory $\vec{d}_p$. This can have the effect of an improved visualization of a percutaneous intervention.

In order to obtain a corresponding determination of the MR planes 41, 42, 43, for example, it can be possible to initially implement a determination of these planes using the Equations 1 through 6 that are discussed above, and in a further step to implement an alignment of the MR planes 41, 42, 43 that are determined in such a manner on the reference point 51 or, respectively, the target point 11 of the trajectory $\vec{d}_p$ by means of a linear coordinate shift. In the following equations, $\vec{g}$ designates an original center of one of the MR planes 41, 42, 43, and $\vec{g}_0$ designates either the reference point 51 or the target point 11 of the trajectory $\vec{d}_p$, and $\vec{g}_{new}$ designates the new center of the accordingly transformed MR plane 41, 42, 43—thus for instance the center 42A of the second MR plane 42, or the center 43A of the third MR plane 43. In an alignment of the corresponding MR plane on the reference point 51 or the target point 11 by means of the following coordinate shift, it can then take place that:

$$\vec{g}_{new} = \vec{g} + \mu \vec{r} + \xi \vec{c} \quad (7),$$

$$\mu = (\vec{g} - \vec{g}_0)^T \cdot \vec{r} \quad (7a),$$

$$\xi = (\vec{g} - \vec{g}_1)^T \cdot \vec{c} \quad (7b).$$

Figure 6:
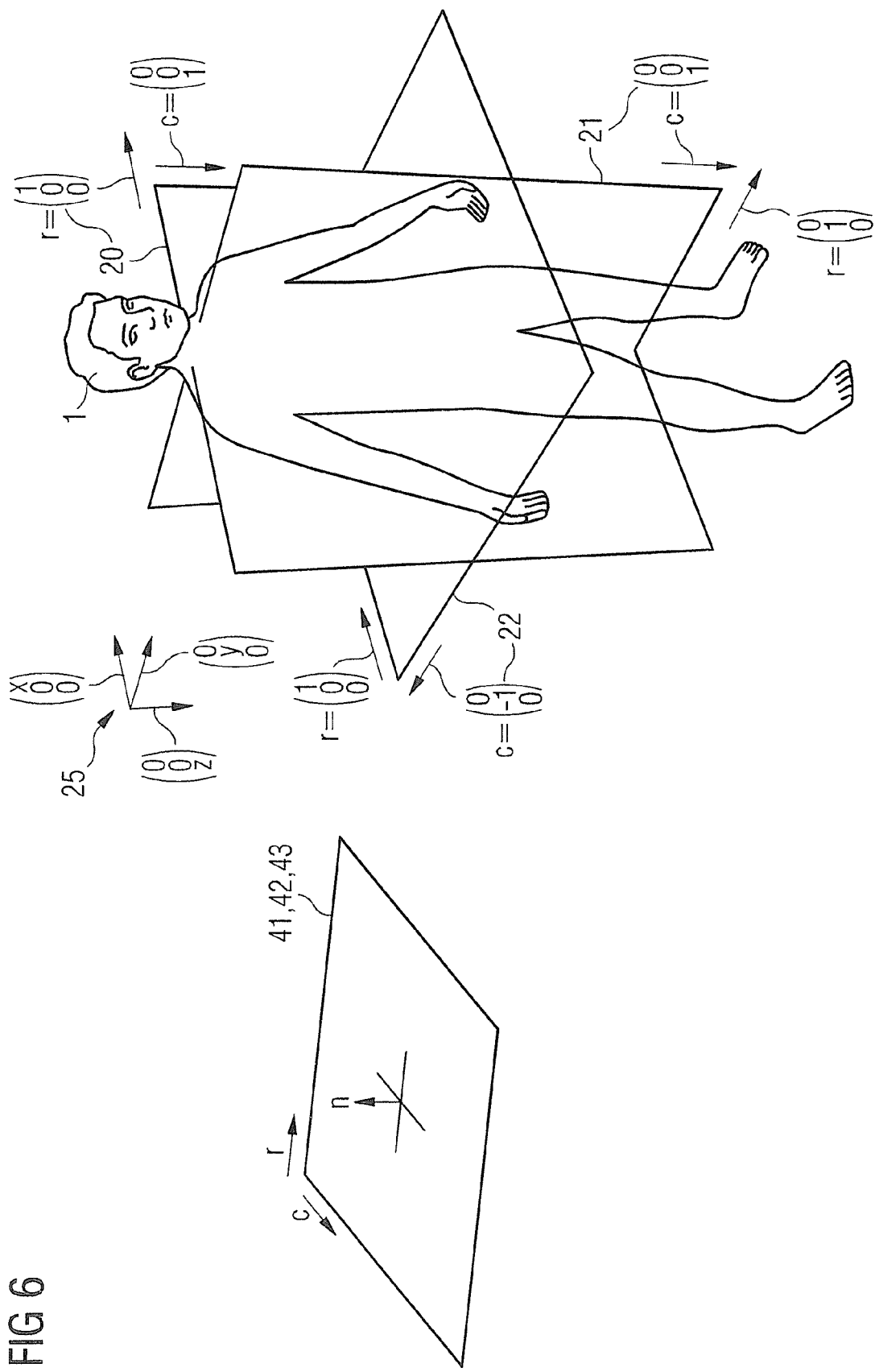
FIG. 6 illustrates a lateral orientation of a reference plane or an imaging plane based on the use of row, column and normal vectors and a reference coordinate system.

In these equations, the vectors r and c designate the row and column vectors as they are defined in a corresponding coordinate system relative to the lateral orientation (i.e. the orientation within the plane) of one of the MR planes 41, 42, 43. This is illustrated on the left side in FIG. 6. For example, the association of specific directions with row or column or normal vectors (r-, c-, n-vectors) can be used to determine the lateral orientation of images that are acquired by means of MRT for the corresponding MR plane 41, 42, 43.

The lateral orientation can take place with a lateral orientation of the reference planes, thus the anatomical planes 20, 21, 22. An illustrative association of the row and column vectors r, c, with the different anatomical planes 20, 21, 22 in the reference coordinate system 25 is illustrated on the right side in FIG. 6. In particular, the determination of one or more of the MR planes 41, 42, 43 can then take place such that the lateral orientation is matched to the lateral orientation of one or more of the anatomical planes 20, 21, 22 for which a clearance relative to the corresponding MR plane 41, 42, 43 is minimal.

For example, with reference to FIG. 3 the lateral orientation—i.e. the association with row and column vectors r, c—of the first MR plane 41 can be in correspondence with the lateral orientation of the transverse plane 22. For example, if a determination of the alignment of the MR planes 41, 42, 43 initially takes place by means of Equations 1-6, in a subsequent step the lateral orientation can take place by means of an alignment using a coordinate rotation of the MR planes 41, 42, 43 at the correspondingly associated anatomical planes 20, 21, 22. Corresponding methods of coordinate rotation are known to those skilled in the art, such that no additional details must be cited here.

Figure 7:
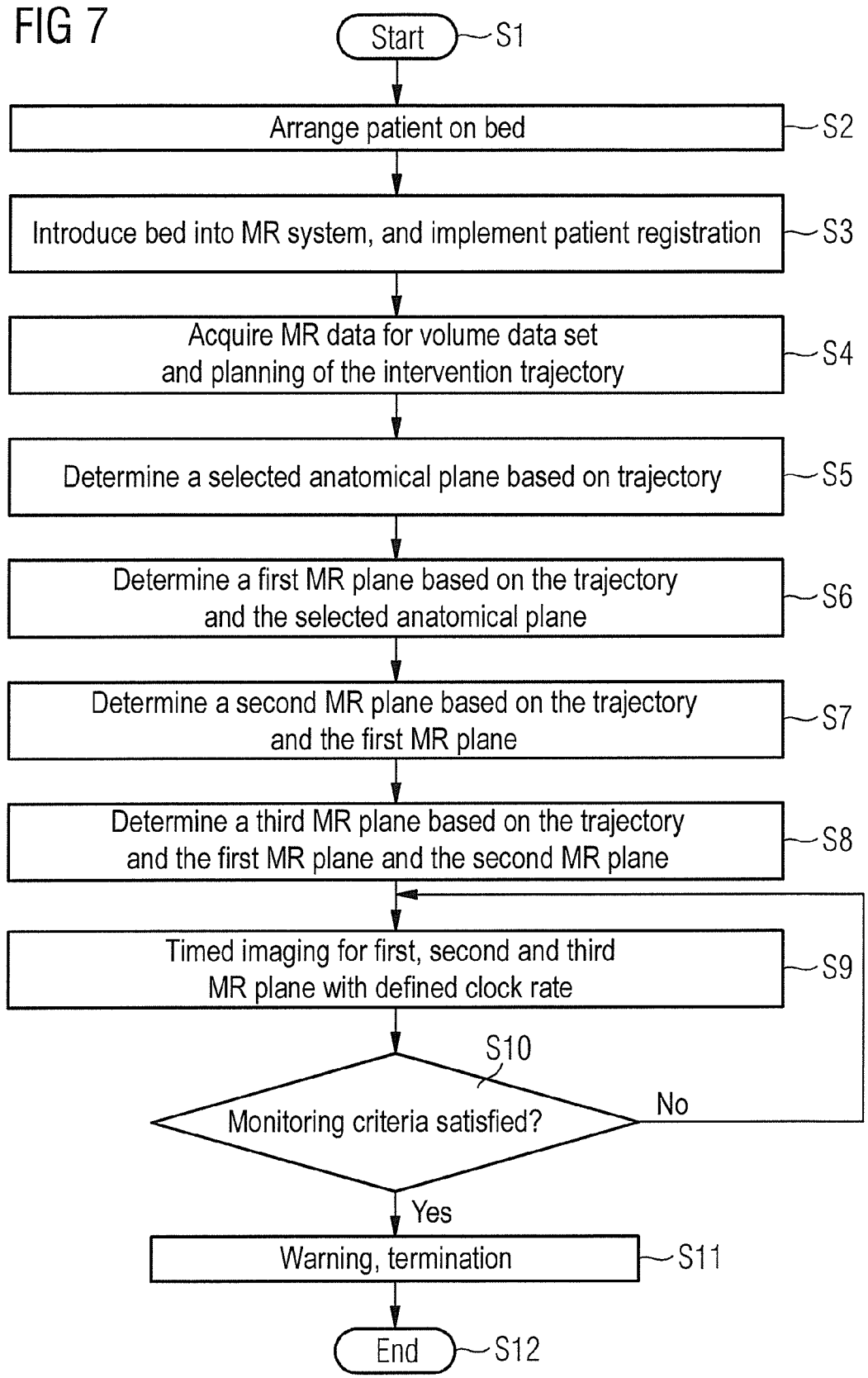
FIG. 7 is a flowchart of a method according to an aspect of the present invention.

FIG. 7 is a flow chart of a method to determine imaging planes for an imaging method to visualize a percutaneous intervention, i.e. to determine MR planes in the case of MRT. Furthermore, the flow chart in FIG. 7 concerns a method to visualize the percutaneous intervention.

The method begins in Step S1. In Step S2, a patient is arranged on a bed, thus for instance the examined person 1 on the table 105. In Step S3, the bed or, respectively, the table 105 is introduced into the MR system 100 and a patient registration is implemented. For example, the patient registration can be implemented by means of the laser positioning system 106. The patient registration serves to set the reference coordinate system 25 (which is defined based on the examined person 1) in relation to the coordinate system 111 of the MR system 100. The patient can then be positioned so that both imaging by means of MRT is possible on the one hand and the percutaneous intervention at the appertaining location can be implemented on the other hand.

The acquisition of MR data for the volume data set 50 and the planning of the trajectory $\vec{d}_p$ of the percutaneous intervention using the volume data set 50 take place in Step S4.

The determination of a selected anatomical plane from the anatomical planes 20, 21, 22 subsequently takes place in Step S5 based on the trajectory $\vec{d}_p$ determined in Step S4. For example, that one of the anatomical planes 20, 21, 22 can be selected which has a minimum clearance relative to the trajectory $\vec{d}_p$, thus that encloses a minimum angle with said trajectory $\vec{d}_p$, for instance.

The determination of the first MR plane 41 takes place in Step S6 based on the trajectory $\vec{d}_p$ and the selected anatomical plane from Step S5. Steps S5 and S6 were discussed in the preceding with reference to FIG. 3.

The determination of the second MR plane 42 and the third MR plane 43 respectively take place in Step S7 and S8. The second MR plane 42 is based on the trajectory $\vec{d}_p$ and the first MR plane 41, while the third MR plane 43 is based on the trajectory and the first and second MR planes 42, 43. Steps S7 and S8 were discussed in detail in the preceding with regard to FIG. 4.

The timed imaging by means of MRT takes place in Step S9 for the first, second and third MR planes 41, 42, 43. For this, MR data are acquired for the MR planes 41, 42, 43 and output as an image. For example, the timed imaging can be implemented during the implementation of a percutaneous intervention. The timed imaging can be implemented with a defined clock rate or clock period. In particular, it is possible that the clock period is selected so that successively acquired magnetic resonance data of different magnetic resonance planes 41, 42, 43 are acquired with a time offset that is smaller than a longitudinal relaxation time of a nuclear magnetization. In such a case, saturation bands can arise along the intersection lines between the MR planes 41, 42, 43, which saturation bands can be used to visualize the percutaneous intervention. These intersection lines can include the trajectory $\vec{d}_p$ and/or the target point 11.

In Step S10 a check is made as to whether a monitoring criterion is satisfied. For example, given simultaneous implementation of the percutaneous intervention it can be monitored whether a signal deviation of the MR data is established in the third MR plane 43. Such a signal deviation can be assessed as an indicator that the needle 120 has reached the target point 11 of the trajectory $\vec{d}_p$. Furthermore, it can be monitored whether the sensitive subject 12 (as it was discussed in FIG. 2) has possibly been reached due to movement artifacts or other displacements at the trajectory $\vec{d}_p$. Furthermore, it can be monitored whether a susceptibility artifact is detected on the trajectory $\vec{d}_p$ in the acquired MR data of the first and/or second MR plane 41, 42. Such a susceptibility artifact can be assessed as an indicator of the presence of the needle 120 at the corresponding location along the trajectory $\vec{d}_p$.

If it is established in Step S10 that such a monitoring criterion is not satisfied, Step S9 is implemented further. Otherwise, for example, a warning or a termination of the imaging taking place in Step S11 occurs, or other suitable measures are taken. The method ends in Step S12.

Figure 8:
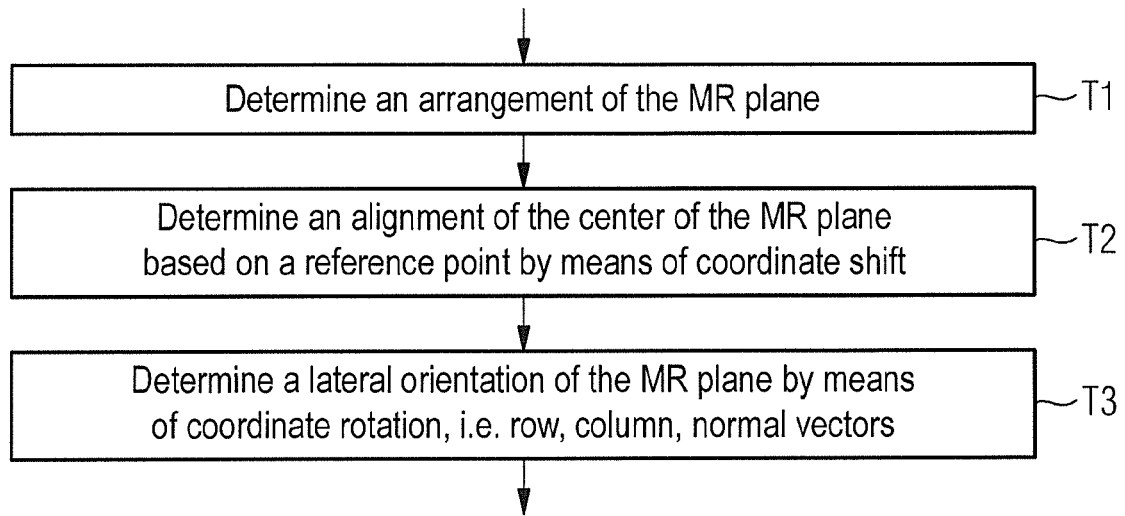
FIG. 8 is a flowchart of the method from FIG. 7 that depicts the determination of MR planes in more detail.

Steps S6, S7 and S8 of FIG. 7—i.e. the determination of the first, second and third MR planes 41, 42, 43—are explained in detail in FIG. 8. The determination of the MR planes 41, 42, 43 can initially (in Step T1) include the determination of an arrangement of the corresponding plane 41, 42, 43. This can designate an arrangement in space, for example relative to the reference coordinate system 25 of the examined person 1 or, respectively, to the anatomical planes 20, 21, 22. The determination of the arrangement of the corresponding MR plane in Step T1 can correspond to the calculation of the vectors $\vec{V}$ spanning the plane according to one of the Equations 2-6.

Furthermore, each or any MR plane 41, 42, 43 determined in Step T1 can have a finite lateral extent, and therefore a center. The alignment of the center of the MR plane determined in Step T1 takes place in Step T2, based on the reference point 51 of the volume data set 50. Step T2 can include a coordinate shift according to one of the Equations 7, 7a and 7b. It is also possible that an alignment does not occur at the reference point 51, but rather at other relevant points, for instance the start point 10 or the target point 11 of the trajectory $\vec{d}_p$ or at a point of a sensitive organ etc. In such cases, the alignment can have the effect that an improved and comprehensive visualization of the percutaneous intervention is achieved.

A lateral orientation of the MR plane of Steps T1 and T2 can be determined in Step T3, i.e. a rotation of the MR plane, for example. Step T3 can include a coordinate rotation. The lateral orientation of the MR plane can be provided by the use of row, column and normal vectors r, c, n.

Figure 9:
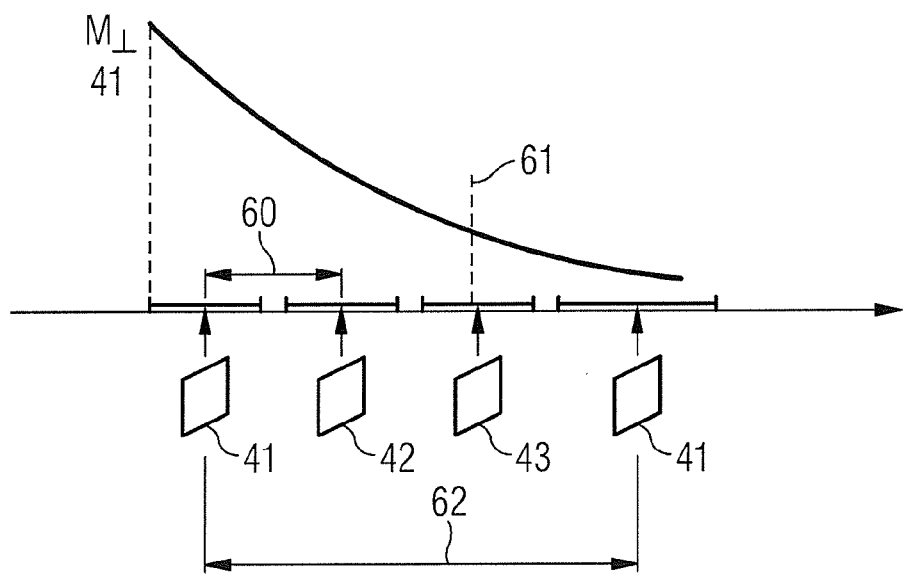
FIG. 9 schematically illustrates the timed acquisition of MR data with regard to a longitudinal relaxation time of a nuclear magnetization.

In FIG. 9, the visualization of a percutaneous intervention is represented by means of timed acquisition of MR data for the MR planes 41, 42, 43. The transversal magnetization of 1-H nuclei for the plane 41 is plotted over time. After exciting the transversal magnetization to acquire MR data from the first MR plane 41 at the beginning of the clock period 62, the transversal magnetization relaxes back into the steady state, i.e. parallel to the longitudinal direction that is defined by the basic magnetic field. In FIG. 9, this is represented by the straight line that illustrates an exponential relaxation. This occurs on a characteristic time scale that is defined by a longitudinal relaxation time 61. A time offset 60 is indicated between the acquisition of the MR data for the first MR plane 41 and the acquisition of the MR data for the second MR plane 42. In particular, the time offset 60 is shorter than the longitudinal relaxation time 61.

The clock period 62 designates the time between successive acquisitions of MR data from the first MR plane 41. The clock period 62 is dependent on the technical boundary conditions of the MRT. For example, the clock period 62 can be dependent on the MR acquisition sequence that is used. In one embodiment, for example, the MR acquisition sequence can be a "Balanced True FISP" acquisition technique as it is known to those skilled in the art. Clock period 62 can then amount to 0.5 seconds to 1 second, for example. The time offset 60 can accordingly enable an acquisition frequency of MR data from the different MR planes 41, 42, 43 with two to five images per second. The clock period or the acquisition frequency directly depends on the MR acquisition sequence that is used. For example, there are particularly fast MR acquisition sequences that enable a particularly fast imaging, for example via use of multiple coils with different positional space sensitivities and an undersampling of the positional frequency space (k-space). Such MR acquisition sequences are known to those skilled in the art as "SENSE", "SMASH" and "GRAPPA". The applicability of the present invention is not limited to such accelerated MR acquisition sequences.

Although modifications and changes may be suggested by those skilled in the art, it is the intention of the inventor to embody within the patent warranted hereon all changes and modifications as reasonably and properly come within the scope of her contribution to the art.

I claim as my invention:

1. A computerized method to automatically determine imaging planes in an imaging procedure to visualize a percutaneous intervention of a patient whom an instrument proceeds along a trajectory within the patient from a starting point to a target point within the patient while the patient is situated in an imaging apparatus, said method comprising:

providing reference coordinate system data to a processor that represent a reference coordinate system of the patient, said reference coordinate system data defining three orthogonal reference planes of said reference coordinate system;

providing said processor with trajectory data representing the spatial arrangement of said trajectory and said target point, said trajectory having a defined spatial arrangement between said starting point and said target point in relation to said reference planes;

in said processor, automatically selecting one of said reference planes as a selected reference plane based on the arrangement of the reference planes relative to the trajectory;

in said processor, defining a first imaging plane such that said trajectory lies in said first imaging plane, and such that said first imaging plane has a defined spatial arrangement in relation to the selected reference plane;

in said processor, defining a second imaging plane such that the trajectory also lies in said second imaging plane and such that said second imaging plane is orthogonal to said first imaging plane;

in said processor, defining a third imaging plane such that said third imaging plane is orthogonal to said first imaging plane and is orthogonal to said second imaging plane, and such that said third imaging plane comprises said target point; and from said processor, generating and emitting an electrical signal in a format to operate said imaging apparatus in order to acquire image data from the patient in said first, second and third imaging planes, said image data comprising data that visually represent said trajectory between said starting point and said target point.

2. A method as claimed in claim 1 comprising providing said reference coordinate system data to said processor with said three orthogonal planes respectively being a transverse plane, a sagittal plane and a frontal plane of said patient examined person.

3. A method as claimed in claim 1 comprising determining said first imaging plane such that a plane normal of said first imaging plane is parallel to a component of a plane normal of the selected reference plane that is perpendicular to said trajectory.

4. A method as claimed in claim 1 comprising determining said first imaging plane such that said first imaging plane has a minimized clearance with said selected reference plane.

5. A method as claimed in claim 4 wherein said clearance is an angle between said first imaging plane and said selected reference plane.

6. A method as claimed in claim 1 comprising determining a clearance in said processor for at least two of the reference planes relative to said trajectory, and determining said selected reference plane dependent on the calculated clearance.

7. A method as claimed in claim 6 wherein said clearance is an angle between said trajectory and said at least two of said reference planes.

8. A method as claimed in claim 1 comprising providing said reference coordinate system data to said processor that represent a lateral orientation of said reference planes, and determining at least one of said first, second and third imaging planes so as to have a lateral orientation based on the lateral orientation of one of said reference planes for which a clearance with respect to said at least one imaging plane is minimized.

9. A method as claimed in claim 8 wherein said clearance is an angle between said one of said reference planes and said at least one imaging plane.

10. A method as claimed in claim 6 comprising aligning, with respect to a coordinate system, said lateral orientation of said at least one imaging plane on the lateral orientation of the reference plane for which said clearance is minimal.

11. A method as claimed in claim 10 wherein said clearance is an angle between said at least one imaging plane and said reference plane.

12. A method as claimed in claim 1 comprising:
providing said processor with a volume data set that includes said trajectory and determining, in said processor, a reference point in said volume data set; and
determining at least one of said first, second and third imaging planes to have a center that is aligned on said reference point.

13. A method as claimed in claim 12 comprising, in said processor, executing a linear coordinate displacement to align said center of said at least one of said imaging planes on said reference point.

14. A method as claimed in claim 1 comprising determining said third imaging plane so as to have a center aligned on said target point.

15. A method as claimed in claim 14 comprising, in said processor, implementing a linear coordinate displacement to align said center of said third imaging plane on said target point.

16. A method as claimed in claim 1 comprising providing said trajectory data to said processor in a volume data set acquired from said examined person, said volume data set including said trajectory, and wherein said volume data set and said trajectory have a defined spatial arrangement relative to said reference planes.

17. A method as claimed in claim 1 comprising providing said trajectory data as data representing a position of a needle as said instrument in said percutaneous intervention.

18. A method as claimed in claim 1 wherein said imaging apparatus is a magnetic resonance tomography apparatus, and said method comprising:
acquiring magnetic resonance data from said patient in said first, second and third imaging planes, said magnetic resonance data including magnetic resonance trajectory data as said data representing said trajectory, in a plurality of magnetic resonance data acquisitions with a clock period; and
providing said magnetic resonance data to a display device in communication with said processor and, at said display device, presenting said visualization of said percutaneous intervention as two-dimensional, real-time magnetic resonance images in which said first, second and third reference planes are first, second and third magnetic resonance planes.

19. A method as claimed in claim 18 comprising acquiring said magnetic resonance data with said clock period being smaller than a longitudinal relaxation time of nuclear spins that produce said magnetic resonance data.

20. A method as claimed in claim 18 comprising implementing an automatic monitoring of said visualization of said percutaneous intervention to identify an occurrence of at least one event selected from the group consisting of a signal deviation of said magnetic resonance data of said third magnetic resonance plane, a sensitive object in said examined person on said trajectory in either of said first or second magnetic resonance planes, and a susceptibility artifact on said trajectory in either of said first or second magnetic resonance planes.

21. A magnetic resonance system to automatically determine imaging planes in an imaging procedure to visualize a percutaneous intervention of a patient who an instrument proceeds along a trajectory within the examined person from a starting point to a target point within the examined person, said system comprising:
a magnetic resonance data acquisition unit;
a processor provided with reference coordinate system data that represent a reference coordinate system of the patient, said reference coordinate system data defining three orthogonal reference planes of said reference coordinate system;
said processor being provided with trajectory data, acquired by said data acquisition unit, representing the spatial arrangement of said trajectory and said target point, said trajectory having a defined spatial arrangement between said starting point and said target point in relation to said reference planes;
said processor being configured to automatically select one of said reference planes as a selected reference plane based on the arrangement of the reference planes relative to the trajectory;
said processor being configured to define a first imaging plane such that said trajectory lies in said first imaging plane, and such that said first imaging plane has a defined spatial arrangement in relation to the selected reference plane;

said processor being configured to define a second imaging plane such that the trajectory also lies in said second imaging plane and such that said second imaging plane is orthogonal to said first imaging plane;

said processor being configured to define a third imaging plane such that said third imaging plane is orthogonal to said first imaging plane and is orthogonal to said second imaging plane, and such that said third imaging plane comprises said target point; and said processor being configured to generate and emit an electrical signal in a format to operate said imaging apparatus in order to acquire image data from the patient in said first, second and third imaging planes, said image data comprising data that visually represent representing said trajectory between said starting point and said target point.

22. A magnetic resonance system as claimed in claim 21 wherein said processor is configured to operate said data acquisition unit to acquire said magnetic resonance data in a plurality of magnetic resonance data acquisitions with a clock period; and wherein said magnetic resonance system comprises a display device in communication with said processor provided with said magnetic resonance data, and said display device being configured to present said visualization of said percutaneous intervention as two-dimensional, real-time magnetic resonance images in which said first, second and third reference planes are first, second and third magnetic resonance planes.

23. A magnetic resonance system as claimed in claim 22 wherein said processor is configured to operate said magnetic resonance data acquisition unit to acquire said magnetic resonance data with said clock period being smaller than a longitudinal relaxation time of nuclear spins that produce said magnetic resonance data.

* * * * *